United States Patent [19]

Levy et al.

[11] Patent Number: 5,066,373
[45] Date of Patent: Nov. 19, 1991

[54] MONITORING PH IN PHENOL ACETONE

[75] Inventors: Alan B. Levy, Randolph; Stylianos Sifniades, Madison; Lloyd C. Kent, Pompton Lakes, all of N.J.; Dominick Frollini, Jr., Trafford, Pa.

[73] Assignee: Allied-Signal Inc., Morris Township, Morris County, N.J.

[21] Appl. No.: 590,251

[22] Filed: Sep. 28, 1990

[51] Int. Cl.⁵ ............................................. G01N 27/26
[52] U.S. Cl. ................................ 204/153.21; 204/433; 568/798
[58] Field of Search ........................... 204/153.21, 433; 568/798

[56]  References Cited
U.S. PATENT DOCUMENTS

| | | | |
|---|---|---|---|
| 4,310,712 | 1/1982 | Langley | 568/798 |
| 4,447,775 | 5/1984 | Breuker et al. | 324/438 |
| 4,490,565 | 12/1984 | Chang et al. | 568/798 |
| 4,876,397 | 10/1989 | Knifton et al. | 568/798 |

Primary Examiner—John F. Niebling
Assistant Examiner—William T. Leader

[57] ABSTRACT

Monitoring acidity at the ppm level in phenol-acetone-cumene process streams on a continuous basis is accomplished with a standard hydrogen electrode and a double-junction reference electrode with an external body solution comprising phenol, acetone, water, and a tetraalkyl- or tetraarylammonium salt, which provide a time invariant voltage without the necessity of adding any external solvent to the process stream. Phenol/acetone ratios can be varied from 1:10 to 10:1 which encompass the 1:1 ratio produced by the phenol-acetone process. A direct correlation of the electrode potential with the acidity of the medium is obtained. With the aqueous mixture isolated by a low flow ceramic junction from the process stream, no contamination of the process stream occurs.

16 Claims, 3 Drawing Sheets

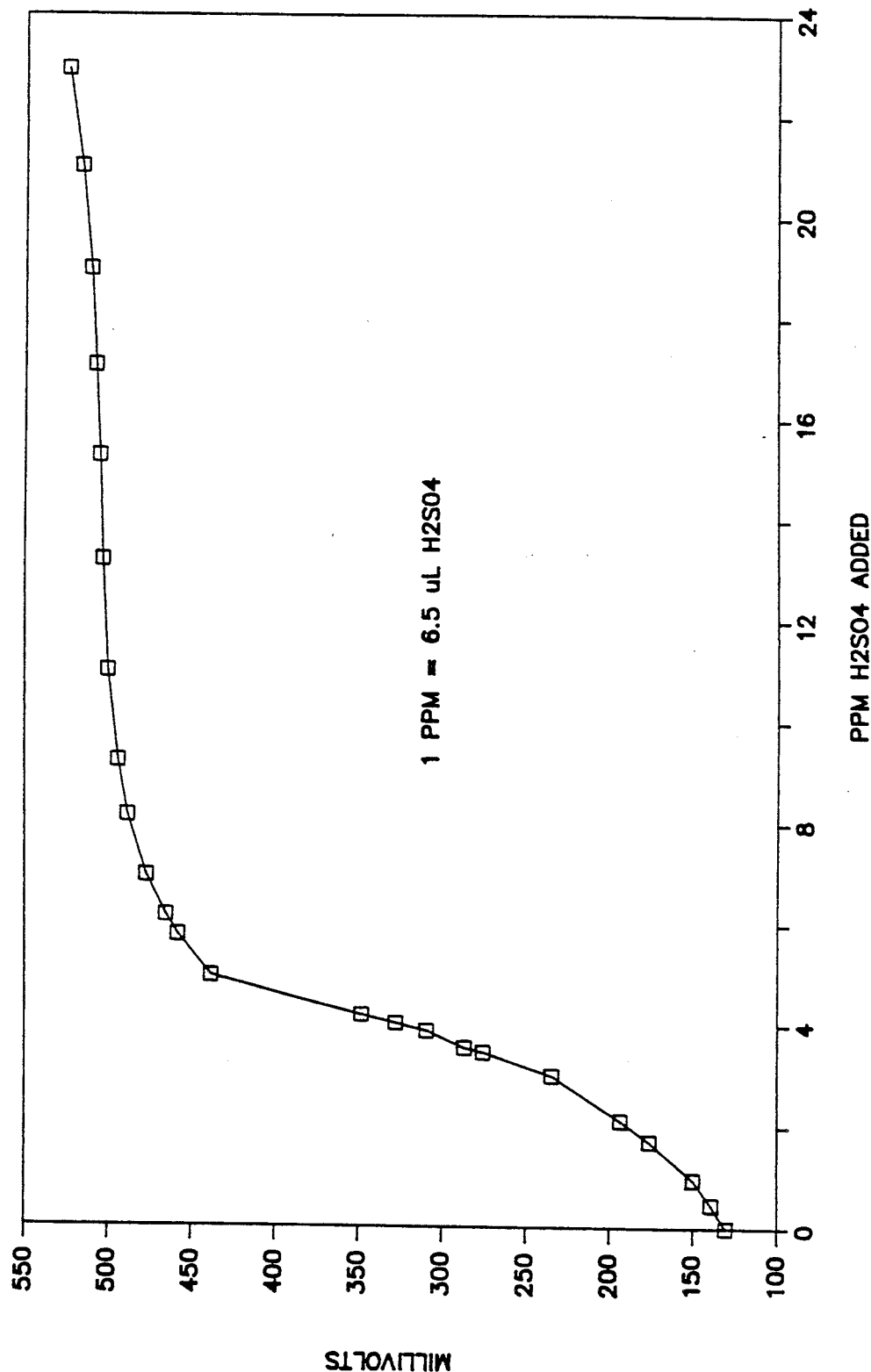

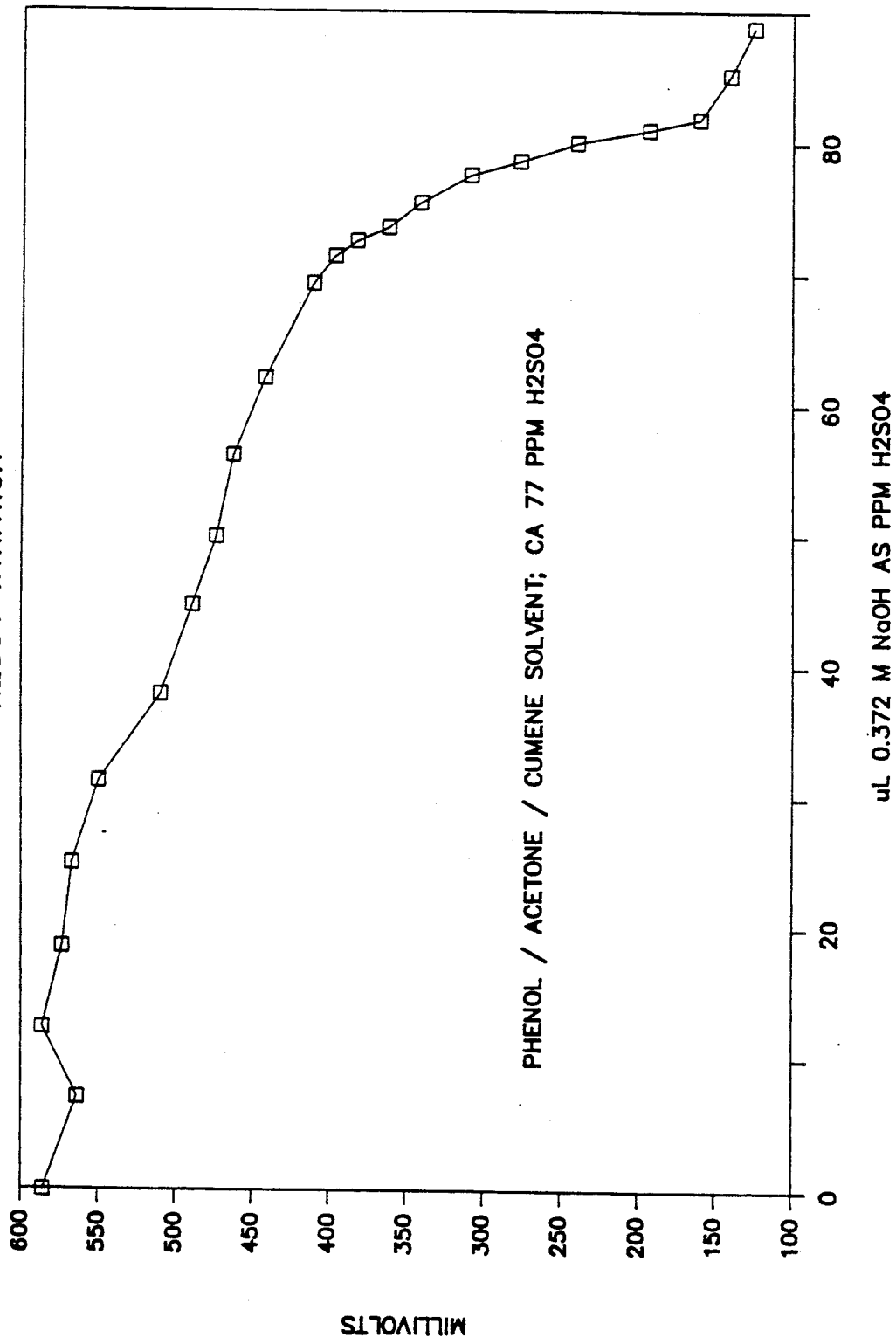

MONITORING PH IN PHENOL ACETONE

BACKGROUND OF THE INVENTION

1. Field of the Invention

This invention relates to the manufacture of phenol by the acid cleavage of cumene hydroperoxide. In particular, this invention relates to controlling acidity levels in phenol-acetone streams in order to produce good quality phenol and to maximize the amount of AMS by-product isolated.

2. Description of Related Art

In general, phenol is prepared by the oxidation of cumene by air, followed by an acid catalyzed cleavage of the resulting cumene hydroperoxide to phenol and acetone. The acid cleavage is typically effected by means of strong inorganic acid, usually sulfuric acid, or by addition of $SO_2$ which may be oxidized in-situ to sulfuric acid. Other suitable inorganic acids include aqueous hydrochloric or perchloric acid. The acid cleavage reaction mixture typically includes primarily phenol, acetone, and cumene. In addition to the principal products, the acid cleavage reaction mixture will further contain varying amounts of minor by-products, principally alpha-methylstyrene, dimethylphenylcarbinol, water, acetophenone, p-cumylphenol and various alpha-methylstyrene dimers. Of these components alpha-methylstyrene is a useful by-product and it is desirable to recover it.

Dimethylphenylcarbinol is relatively unstable and decomposes to alpha-methylstyrene and condensation products under the influence of acidity and/or temperature. The decomposition of dimethylphenylcarbinol produces water and is a reversible reaction. Consequently, it cannot proceed to completion in the presence of water.

In the process of recovering phenol from the acid cleavage reaction mixture, the reaction mixture is initially neutralized, either directly by the addition of a base or indirectly by contact with an ion exchange resin. The neutralized reaction mixture is fed to a distillation train where alpha-methylstyrene, phenol and acetone are recovered. In the early stages of the distillation, water is removed and desirably dimethylphenylcarbinol decomposes to the aforementioned by-products which are removed in subsequent distillation stages.

In this process, a key element is the control of acidity in the effluent stream fed to the distillation columns. If more than 1 or 2 ppm residual inorganic acid is present, a large portion of alpha-methylstyrene is decomposed to alpha-methylstyrene dimers or reacts with phenol to form cumylphenol. On the other hand, if the acidity is too low, dimethylphenylcarbinol doesn't decompose until the phenol still bottoms leading to alpha-methylstyrene contamination of the phenol. The present invention is particularly directed towards controlling the acidity of the neutralized cleavage mixture in order to produce good quality phenol and maximize the isolated yield of by-product alpha-methylstyrene by minimizing its decomposition to side-products.

Present methods for monitoring acidity in phenol-acetone involve diluting the product with water and measuring the resultant pH in the aqueous phase. Because of the necessity of adding water, this approach is complicated and usually run as a batch operation. Such an operation suffers from unduly large time lags between the taking of the sample and reporting the results.

A significant improvement in process control and thus yield of alpha-methylstyrene would involve the direct monitoring of acidity in the phenol-acetone stream. Extensive studies of indicator electrodes and potentiometric titrations in hydrocarbon and related solvents have been made in order to directly monitor the degree of acidity in fuel oils and lubricating oils. The results have been summarized by G. J. Hill in *Reference Electrodes* p433–463 (1961) and references therein. In general, the same electrodes used in aqueous systems are used in nonaqueous systems. Most of the work has been based on a combination of indicator electrode and aqueous reference electrode and contains many instances where the addition of a protic solvent, such as alcohol to the solution to be titrated, was necessary before satisfactory results could be obtained. The necessity of adding an external solvent to a process stream to measure acidity complicates continuous monitoring. Thus, a test side-stream with metering pumps and related control equipment is normally required. Moreover, addition of such solvent would introduce impurities to the process were the test stream to be returned to the process stream. As a result, the test stream is usually disposed of, adding to the cost of the process. Our work also confirmed that standard electrode systems in a phenol-acetone-cumene system in the absence of added water are unsuitable due to instability over time in the voltages observed.

SUMMARY OF THE INVENTION

The present invention is concerned with monitoring acidity at the ppm level in phenol-acetone-cumene process streams and particularly with monitoring such acidity on a continuous basis. We have found that when a standard hydrogen electrode and a double-junction reference electrode with an external body solution comprising phenol, acetone, water, and a tetraalkyl- or tetraarylammonium salt are used a time invariant voltage is observed without the necessity of adding any external solvent to the process stream. Thus a direct correlation of the electrode potential with the acidity of the medium is obtained. Significantly, with the aqueous mixture isolated by a low flow ceramic junction from the process stream, no contamination of the process stream occurs.

BRIEF DESCRIPTION OF THE DRAWINGS

FIG. 2 provides the electrode response to incremental addition of $H_2SO_4$ to a cumene hydroperoxide decomposition mixture.

FIG. 3 provides a titration curve wherein a phenol/acetone/cumene solution with $H_2SO_4$ is neutralized with NaOH.

DETAILED DESCRIPTION OF THE PREFERRED EMBODIMENT

Figure 1:
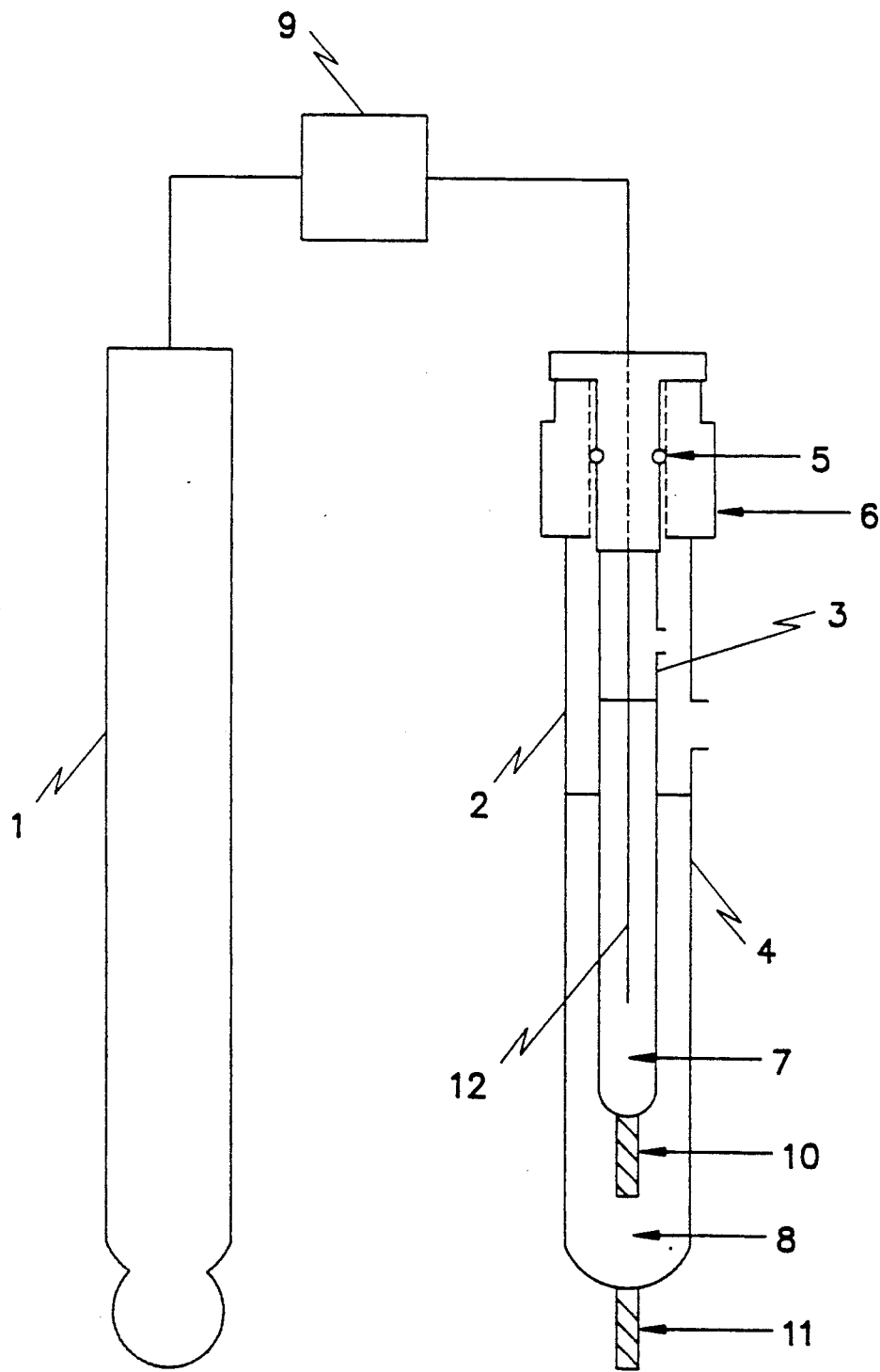
FIG. 1 provides a schematic of the electrode system for monitoring pH in phenol-acetone systems.

With reference to FIG. 1, the invention comprises the use of a standard hydrogen ion electrode 1 in combination with a double junction reference electrode 2.

The double junction reference electrode 2 comprises an inner body 3 sealably engaged with an outer body 4, for example by the O-ring 5 in cooperation with the sleeve 6 illustrated in the figure.

The reference electrode inner body 3 can be filled with a standard reference system electrolyte designated 7, known to those skilled in the art. Such known reference systems include, but are not limited to silver/silver chloride in saturated KCl solution and mercury/calomel in saturated KCl solution, with the silver or mercury referring to the lead-out wire designated 12. A standard 4 molar potassium chloride solution saturated with silver chloride is illustrated in the example. The outer body 4 is filled with a solution designated 8 consisting of a salt dissolved in a solution of phenol, acetone and water. Phenol/acetone ratios can be varied from 1:10 to 10:1 which encompass the 1:1 ratio produced by the phenol/acetone process. The amount of water should be such that the solution is homogeneous. The amount of water can be from 1 weight percent up to the solubility limit of water in phenol/acetone. Preferably the water is present in the amount of 5 to 15 weight percent of the solution. The salt can be any salt which is neutral, soluble and stable in the medium. Preferred salts include tetraalkyl and tetraaryl ammonium halide salts such as, but not limited to, tetramethylammonium chloride, tetramethylammonium bromide, tetramethylammonium iodide, tetraethylammonium chloride, tetraethylammonium bromide, tetraethylammonium iodide, tetraphenylammonium chloride, tetraphenylammonium bromide and tetraphenylammonium iodide. Also, tetra-n-butylammonium chloride, tetra-n-butylammonium bromide and tetra-n-butylammonium iodide are contemplated. Concentrations of this salt can vary from 0.02 weight percent to saturation and will vary depending on the nature of the salt and according to temperature.

The standard hydrogen ion electrode 1 and double junction reference electrode 2 are connected to pH meter 9, a standard pH meter capable of reading output in millivolts, which measures the potential difference between the two electrodes. Sintered ceramic junctions 10 and 11 permit flow of solution from the inner body to the outer body and from the outer body to the process stream being monitored during operation of the electrodes. Accordingly, it may be preferred to select low flow, fine ceramic junctions 10 and 11 to minimize flow. During operation, the electrodes are immersed in the phenol/acetone process stream to be monitored (not shown).

The invention will be demonstrated by the following examples, but it should not be construed as limited to these examples.

EXAMPLE 1

A two electrode system comprising a standard hydrogen electrode and a double junction silver/silver chloride electrode was used. The inner body of the reference electrode was filed with 4 Molar potassium chloride saturated with silver chloride. The outer body solution comprised 20.57 g of 1:1 M phenol/acetone, 2.43 g $H_2O$ and 0.0510 g of tetra-n-butylammonium chloride. The probes were standardized by use of two buffer solutions. The first consisted of a mixture of 5.90 g tetra-n-butylammonium acetate, 1.18 g acetic acid, 155.84 g of 1:1 molar phenol/acetone and 1.68 g water. The response of the probes was arbitrarily fixed at ca 134 mv. Under these conditions, a second buffer consisting of 2.73 g tetra-n-butylammonium acetate, 11.68 g acetic acid, 116.56 g 1:1 molar phenol/acetone and 1.23 g of water gave a reproducible response of 240 mv demonstrating that the probes are functioning. The probes were next immersed in a simulated cumene hydroperoxide decomposition mixture consisting of 30.44 g 1:1 molar phenol/acetone, 4.83 g cumene, and 0.356 g water. Addition of incremental amounts of aqueous sulfuric acid gave the response shown in FIG. 2. These results demonstrate that the electrode response is ca 55 millivolts per ppm of sulfuric acid up to ca 6 ppm of acid. Desired residual acidity in the neutralized acid cleavage mixtures is generally below 2 ppm of sulfuric acid. Therefore, the system can be used to monitor the acidity of said mixtures.

EXAMPLE 2

The two electrode system was prepared and calibrated according to Example 1. A solution consisting of 0.292 g of 0.0753 M aqueous sulfuric acid mixed with 28.757 g of phenol/acetone (1:1 on a molar basis) was prepared. The electrodes were immersed in this solution and allowed to equilibrate for 15 minutes. To this mixture was added in incremental amounts 2-10 uL of 0.3716 M sodium hydroxide. The resultant titration curve is shown in FIG. 3. These results demonstrate that the electrode system can be used to titrate residual acid in phenol/acetone mixtures without the necessity of diluting said mixtures with large amounts of water or other protic solvent.

WHAT IS CLAIMED:

1. In a process for producing phenol by oxidation of cumene to cumene hydroperoxide followed by an acid catalyzed cleavage of cumene hydroperoxide to an acid cleavage reaction mixture comprising phenol, acetone, alpha-methylstyrene, and cumene, then neutralizing said acid cleavage reaction mixture followed by distillation to recover phenol, said neutralized acid cleavage reaction mixture containing 0-5 weight percent water; the method of monitoring said neutralized acid cleavage reaction mixture for acidity comprising:

immersing a standard hydrogen ion electrode and a double-junction reference electrode in said neutralized acid cleavage reaction mixture and measuring the potential difference between the two electrodes to determine level of acidity;

said double junction reference electrode comprising an inner body containing an inner body solution comprising a standard reference system electrolyte; an outer body containing a homogeneous outer body solution comprising a salt dissolved in a solution of phenol, acetone and water, the phenol to acetone molar ratio being from 1:10 to 10:1, the water being present in an amount of at least 1 weight percent, said salt selected to be neutral, soluble and stable in said outer body solution; a portion of said inner body being immersed in said outer body solution; first junction means disposed on said inner body to permit flow from said inner body to said outer body and second junction means disposed on said outer body to permit flow from said outer body to said neutralized acid cleavage reaction mixture.

2. The process of claim 1 wherein said salt in said outer body solution is at least 0.02 weight percent tetraalkyl or tetraaryl ammonium halide salt.

3. The process of claim 2 wherein said salt is selected from the group consisting of tetramethylammonium chloride, tetramethylammonium bromide, tetramethylammonium iodide, tetraethylammonium chloride, tetraethylammonium bromide, tetraethylammonium iodide, tetraphenylammonium chloride, tetraphenylammonium bromide and tetraphenylammonium iodide.

4. The process of claim 3 wherein said outer body solution comprises 5 to 15 weight percent water.

5. The process of claim 2 wherein said salt is selected from the group consisting of tetra-n-butylammonium chloride, tetra-n-butylammonium bromide, and tetra-n-butylammonium iodide.

6. The process of claim 5 wherein said salt in said outer body solution is tetra-n-butylammonium chloride.

7. The process of claim 6 wherein said outer body solution comprises 5 to 15 weight percent water.

8. The process of claim 7 wherein said inner body solution is a standard 4M potassium chloride solution saturated with silver chloride.

9. The method of monitoring acidity in an organic mixture comprising phenol and acetone and 0 to 5 weight percent water comprising immersing a standard hydrogen ion electrode and a double junction reference electrode in said organic mixture and measuring the potential difference between the two electrodes to determine level of acidity;

said double junction reference electrode comprising an inner body containing an inner body solution comprising a standard reference system electrolyte; an outer body containing a homogeneous outer body solution comprising a salt dissolved in a solution of phenol, acetone and water, the phenol to acetone molar ratio being from 1:10 to 10:1, the water being present in an amount of at least 1 weight percent, said salt selected to be neutral, soluble and stable in said outer body solution; a portion of said inner body being immersed in said outer body solution; first junction means disposed on said inner body to permit flow from said inner body to said outer body and second junction means disposed on said outer body to permit flow from said outer body to said organic mixture.

10. The method of claim 9 wherein said salt in said outer body solution is at least 0.02 weight percent tetraalkyl or tetraaryl ammonium halide salt.

11. The method of claim 10 wherein said salt is selected from the group consisting of tetramethylammonium chloride, tetramethylammonium bromide, tetramethylammonium iodide, tetraethylammonium chloride, tetraethylammonium bromide, tetraethylammonium iodide, tetraphenylammonium chloride, tetraphenylammonium bromide and tetraphenylammonium iodide.

12. The method of claim 11 wherein said outer body solution comprises 5 to 15 weight percent water.

13. The method of claim 10 wherein said salt is selected from the group consisting of tetra-n-butylammonium chloride, tetra-n-butylammonium bromide, and tetra-n-butylammonium iodide.

14. The method of claim 13 wherein said salt in said outer body solution is tetra-n-butylammonium chloride.

15. The method of claim 14 wherein said outer body solution comprises 5 to 15 weight percent water.

16. The method of claim 15 wherein said inner body solution is a standard 4 M potassium chloride solution saturated with silver chloride.

* * * * *